(12) United States Patent
Pagé et al.

(10) Patent No.: US 6,391,913 B1
(45) Date of Patent: May 21, 2002

(54) DERIVATIVES OF PACLITAXEL, METHOD FOR PRODUCING SAME AND USES THEREOF

(75) Inventors: Michel Pagé, Québec; Cyrille Bicamumpaka, Quebec; Abdelilah Benosman, Sainte-Foy, all of (CA)

(73) Assignee: BCM Development Inc., Sainte-Foy (CA)

( * ) Notice: Subject to any disclaimer, the term of this patent is extended or adjusted under 35 U.S.C. 154(b) by 0 days.

(21) Appl. No.: 09/409,623

(22) Filed: Oct. 1, 1999

Related U.S. Application Data

(63) Continuation-in-part of application No. 09/108,585, filed on Jul. 1, 1998, now Pat. No. 5,981,564.

(51) Int. Cl.⁷ ..................... A61K 31/337; G07D 305/14
(52) U.S. Cl. ........................................ 514/449; 549/511
(58) Field of Search ........................... 549/511; 514/449

(56) References Cited

PUBLICATIONS

Borman et al.. 1994, C & EN, 21:32–4.
Cardellina II, 1991, J Liq Chromatogr 14:659–65.
Deutsch et al., 1989, J Med Chem, 32:788–92.
Haldar et al., 1997, Cancer Res, 57:229–33.
Kingston, 1991, Pharmac Ther, 52:1–34.
Kingston et al., 1990, J Nat Prod, 53:1–12.
Martin et al., 1990, Cell Tissue Kinet, 23:545–59.
Mathew et al., 1992, J Med Chem, 35:145–51.
Page et al., 1993, Intl J Oncol, 3:473–6.
Rowindky et al., 1990, J Nat Inst, 82:1247–58.
Swindell et al., 1991, J Med Chem, 34:1176–84.
Turgeon et al., 1992, Drug Metabolism and Disposition, 20:762–9.

*Primary Examiner*—T. A. Solola
(74) *Attorney, Agent, or Firm*—Klauber & Jackson

(57) ABSTRACT

The invention relates to new paclitaxel derivatives showing a comparable cytotoxicity of the parent compound, and their uses in a drug targeting therapy. The present invention also relates to the composition and use of such derivative, composition and conjugates for treating cancer.

12 Claims, 3 Drawing Sheets

DERIVATIVES OF PACLITAXEL, METHOD FOR PRODUCING SAME AND USES THEREOF

RELATED APPLICATIONS

This is a continuation-in-part of application Ser. No. 09/108,585 filed on Jul. 1, 1998, now U.S. Pat. No. 5,981,564. The entire content of application Ser. No. 09/108,585 is hereby incorporated by reference.

BACKGROUND OF THE INVENTION (a) Field of the Invention

The invention relates to new paclitaxel derivatives and the use of such paclitaxel derivatives in the synthesis of immunoconjugates, all those compounds aimed for cancer therapy.

(b) Description of Prior Art

Paclitaxel is a natural product extracted from the bark of the Pacific yew (*Taxus brevifolia*). It was thereafter found in other members of the Taxacae family including the yew of Canada (*Taxus canadensis*) found in Gaspesia, eastern Canada and *Taxus baccata* found in Europe whose needles contain paclitaxel and analogs and hence provide a source of paclitaxel and derivatives. The crude extract was tested for the first time during the 60s and its active principle was isolated in 1971 by Wani et al. who at the same time identified its chemical structure. Paclitaxel is a microtubule blocker, but unlike other drugs inhibiting the mitosis by interaction with microtubules such as colchicin, vincristin and podophyllotoxin, paclitaxel does not prevent tubulin assembly. It rather accelerates the tubulin polymerization and stabilizes the assembled microtubules. The drug acts in a unique way that consists in binding to microtubules, preventing their depolymerization under conditions where usually depolymerization occurred (dilution, calcium, cold and microtubules disrupting drugs). Paclitaxel blocks the cell cycle at prophase, which results in an accumulation of cells in G2+M. Because of its unique structure and mechanism of action, paclitaxel is currently used in the treatment of ovarian, breast and non-small cell lung cancers.

Poor solubility of paclitaxel constitutes an important limitation to its administration to cancer patients. To increase paclitaxel availability, total and partial synthesis has been reported. The improvement of paclitaxel solubility was obtained by adjunction of solubilizing functions such as carbonyl or sulfonyl groups with good results. Some of the synthesized products were more active than paclitaxel, many others had a biological activity equivalent or slightly inferior to that of paclitaxel while being far more soluble in water (KINGSTON, D. G., *Pharmacol. Ther.* (England), 52(1) p1–34, 1991).

Paclitaxel has three hydroxyl groups at carbon 1, 7 and 2' susceptible of undergoing an acylation. Their reactivity varies according to the following order: 2'>7>>>1 (MATHEW, A. E., et al., *J. Med. Chem.*, 35, 145–151, 1992). Acylation on 2'C is the best way of paclitaxel modification because of its great reactivity, and because even if 2' acylpaclitaxels loose their property of promoting the microtubules polymerization in vitro, they are hydrolyzed in the cell and revert to paclitaxel and keep their cytotoxic activity (KINGSTON, D. G., et al., *J. Nat. Prod.*, 1–13, 1990; and MELLADO, W., et al., *Biochem. Biophys. Res. Commun.*, 105, 1082–1089, 1984).

Accordingly, to increase solubility and in order to add a functional group that allows the coupling of paclitaxel to a protein carrier, several derivatives have been synthesized by modification of the 2' hydroxyl group.

Chemotherapeutic agents currently used for antitumor therapy are selected for their toxicity towards rapidly proliferating cells. Most of them cause undesirable systemic effects such as cardiac or renal toxicity, marrow aplasia, alopecia, nausea and vomiting. During the last few years, many authors have tried to eliminate these side effects by increasing the availability of the drug to the tumour site. In fact, delivery of the drug can frequently be as important as the activity of the drug itself in providing an effective treatment.

The targeting of drugs to a tumour by antibodies to surface antigens may have considerable implications by increasing the therapeutic index.

Several coupling methods permit the linkage of a cytotoxic drug to a protein that targets a specific antigen expressed by a specific type of cell such as cancer cells. The inventor has described a coupling method of an anti-tumor to an antibody using glutaraldehyde preactivated anti-tumor agent in U.S. Pat. No. 5,208,323, the content of which is hereby incorporated by reference. In that method, an amino group of anticancer drugs such as anthracyclines or daunorubicine is activated with glutaraldehyde. The latter is then bound to specific antibodies for cancer cells. The inventor has already described some soluble derivatives of paclitaxel, among which taxamine has a free amine group that may be activated by glutaraldehyde for coupling.

The principle of this targeting is that once inside the cell the imine bond is lysed by lysosomal enzymes. These may be active on the product if steric hindrance does not prevent its action.

If one attach an active molecule to a longer atom, the steric hindrance will be decreased. Such molecules have been used and commercialized for coupling biotin to macromolecule. Side arms made of C6 to C8 have been used successfully.

It would be highly desirable to be provided with new active paclitaxel derivatives. It would thus be highly desirable to be provided with a drug targeting method to administer new derivatives of paclitaxel for drug targeting cancer treatment.

It would also be highly desirable to be provided with new immunoconjugates to specifically target cancer cells.

SUMMARY OF THE INVENTION

One aim of the present invention is to provide a new active paclitaxel derivative modified at the C-2' position.

Another aim of the present invention is to provide new paclitaxel derivatives, which show cytotoxic activity similar to paclitaxel alone.

Another aim of the present invention is to provide a pharmaceutical composition comprising a derivative as defined above with a pharmaceutically acceptable carrier.

Another aim of the present invention is to provide an immunoconjugate comprising a new paclitaxel derivative conjugated to a carrier molecule.

Another aim of the present invention is to provide a method to conjugate a paclitaxel derivative as defined above to a carrier molecule.

Another aim of the present invention is to provide a method for in vivo treatment or prophylaxis of cancer.

In accordance with the present invention there is provided a new paclitaxel derivative or a salt thereof having the following Formula I:

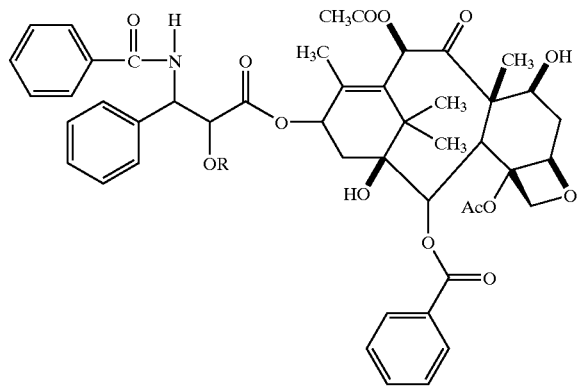

wherein R is a —CO—(CH$_2$)$_{4-8}$—COX, in which X is selected from the group consisting of a hydroxyl, a 1,2-diaminoethenyl, a 1,3-diaminopropyl, a 1,4-diaminobutyl, a 1,5-diaminopentyl, a 1,6-diaminohexyl, and a polar amino acid residue.

Preferably, the polar amino acid residue is selected from the group of residues consisting of arginine, asparagine, aspartic acid, cysteine, glutamic acid, glutamine, glycine, histidine, lysine, phenylalanine, serine, threonine and tyrosine.

In accordance with the present invention, there is also provided a method for the in vivo treatment or prophylaxis of cancer comprising the step of administering a therapeutically effective amount of a new paclitaxel derivative as defined above to a patient in need of such a treatment.

In accordance with the present invention, there is also provided an immunoconjugate having the following formula II:

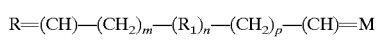

wherein R$_1$ is

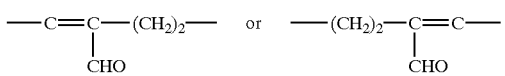

and wherein
  m and p are an integer varying from 0 to 3, with one of m and p being 0;
  n is an integer varying from 1 to 3;
  M is selected from the group consisting of a peptide residue and a protein residue linked to the carbon atom via an amino residue of lysine present therein; and
  R represents a new derivative of paclitaxel as defined above attached at its C-2' position.

In a preferred embodiment of the immunoconjugate of formula II, m is 3 when p is 0 or m is 0 when p is 3.

The method of the present invention as described above can be easily produced and is devoid of significant polymerization.

In accordance with the present invention, there is also provided a method for the in vivo treatment or prophylaxis of cancer comprising the step of administering a therapeutically effective amount of an immunoconjugate comprising a new paclitaxel derivative as defined above to a patient in need of such a treatment.

In accordance with the present invention, there is further provided the use of a derivative as defined previously for the preparation of a medicament for treating cancer.

In accordance with the present invention, there is further provided a method of preparing compounds of Formula II:

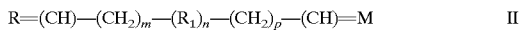

wherein R$_1$ is

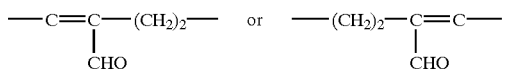

and wherein
  m and p are an integer varying from 0 to 3, with one of m and p being 0;
  n is an integer varying from 1 to 3;
  M is selected from the group consisting of a peptide residue and a protein residue linked to the carbon atom via an amino residue of Lysine present therein; and
  R represents a new derivative of paclitaxel as defined above attached at its C-2' position. The method comprises the steps of:
    a) reacting the new derivative of paclitaxel with glutaraldehyde for obtaining a new paclitaxel derivative glutaraldehyde complex; and
    b) reacting the new paclitaxel derivative glutaraldehyde complex of step a) with a protein or a peptide for obtaining an immunoconjugate.

In order to couple paclitaxel to a carrier molecule, it was then appropriate to synthesize new molecules with long chain (C6–C10) dicarboxylic acid side arms extended by either ethylenediamine, propanediamine, butanediamine, pentanediamine or hexanediamine groups. The final product may then be activated and coupled.

In a preferred embodiment of the invention, M is a protein selected from the group of BCM43 monoclonal antibody, BCM43 humanized antibody, BCM43 chimerized antibody, the (Fab), (Fab)$_2$ or scFv moiety of the BCM43 antibody, BCM17 monoclonal antibody, BCM17 humanized antibody, BCM17 chimerized antibody, the (Fab), (Fab)$_2$ or scFv moiety of the BCM17 antibody, anticarcinoembryonic monoclonal antibody and antialphafetoprotein monoclonal antibody. BCM43 is a monoclonal antibody recognizing an epithelial mucin expressed by ovarian and breast cancer cells. BCM17 (monoclonal anti-P7) is a murine monoclonal antibody recognized a P7 protein, which is overexpressed in resistant ovarian cancer. The hybridoma producing the BCM43 monoclonal antibody was deposited in the International Depositary Authority of Canada in accordance with the Budapest treaty on Sep. 28, 1999, and was given accession number IDAC 280999-1.

In accordance with the present invention, there is provided a method for treating cancer, which comprises administering to a patient a therapeutic dosage of a compound of Formula II as defined previously.

The compound of the present invention may be formulated in a pharmaceutical composition. Such composition, or the compound itself, is preferably used for the preparation of a medicament for treating cancer.

DETAILED DESCRIPTION OF THE INVENTION

Figure 1:
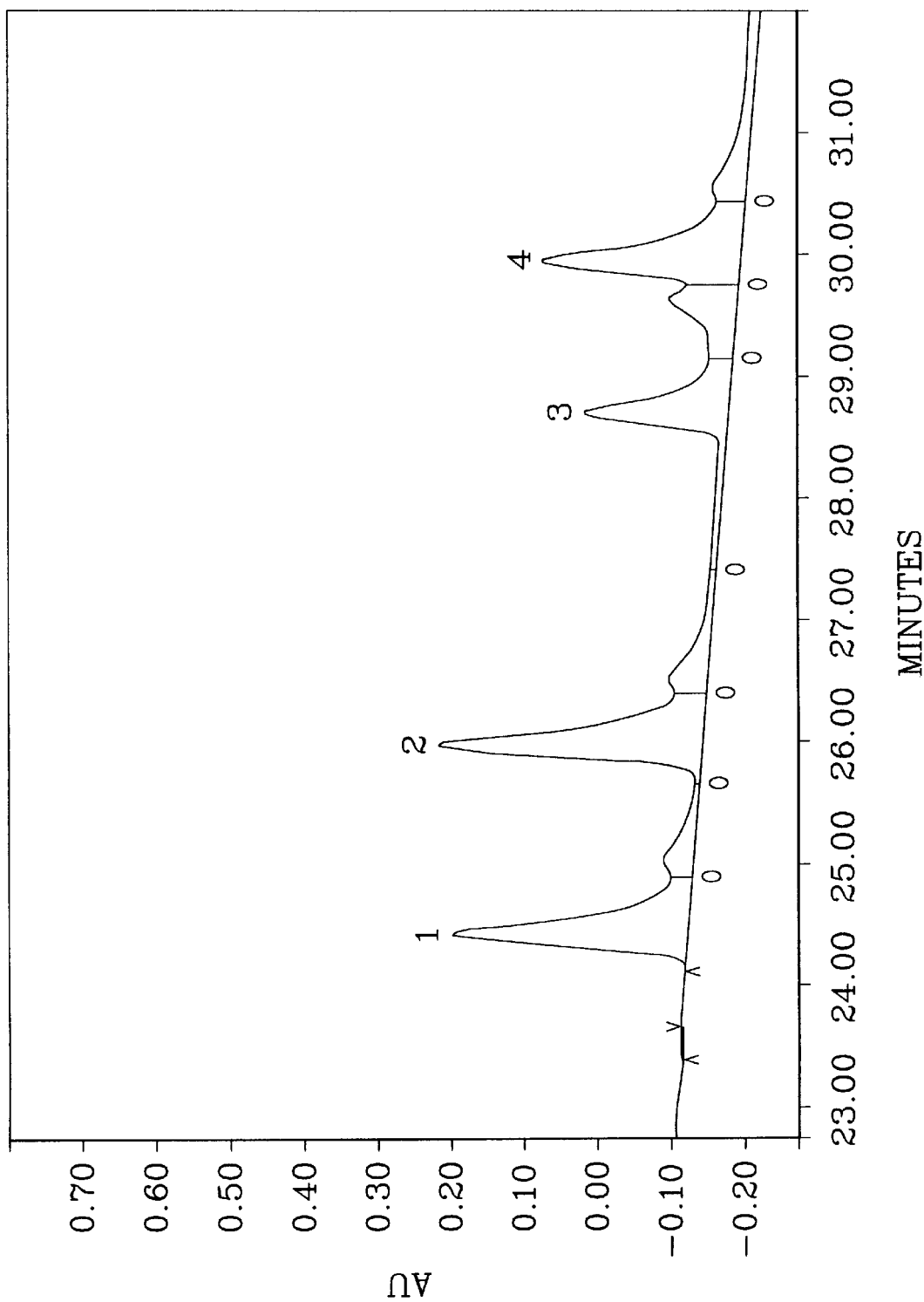
FIG. 1 illustrates a chromatography elution pattern from paclitaxel, 2'-(hexanedioic acid) paclitaxel monoester, 2'-(octanedioic acid) paclitaxel monoester and 2'-(decanedioic acid) paclitaxel monoester.

To increase its bioavailability within a cell, while preserving its cytotoxicity, in accordance with one embodiment of the present invention, there is provided a new paclitaxel derivative substituted at the 2' position of the paclitaxel molecule.

In accordance with a preferred embodiment of the invention, there is provided a new paclitaxel derivative having the following formula:

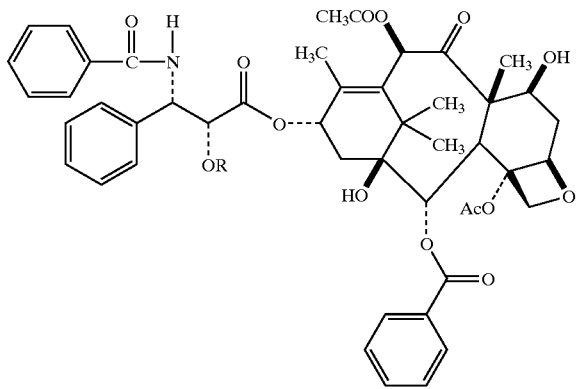

wherein R is defined in Table I below.

TABLE I

| Compound | R |
|---|---|
| 1) 2'-(hexanedioic acid)-paclitaxel monoester (Product 1) | $-CO-(CH_2)_4-COOH$ |
| 2) 2'-(heptanedioic acid)-paclitaxel monoester (Product 2) | $-CO-(CH_2)_5-COOH$ |
| 3) 2'-(octanedioic acid)-paclitaxel monoester (Product 3) | $-CO-(CH_2)_6-COOH$ |
| 4) 2'-(nonanedioic acid)-paclitaxel monoester (Product 4) | $-CO-(CH_2)_7-COOH$ |
| 5) 2'-(decanedioic acid)-paclitaxel monoester (Product 5) | $-CO-(CH_2)_8-COOH$ |
| 6) 2'-[N-(aminoethyl)-amidohexanoic acid]-paclitaxel ester (Taxamine 1) | $-CO-(CH_2)_4-CO-NH-(CH_2)_2-NH_2$ |
| 7) 2'-[N-(aminopropyl)-amidohexanoic acid]-paclitaxel ester (Taxamine 2) | $-CO-(CH_2)_4-CO-NH-(CH_2)_3-NH_2$ |
| 8) 2'-[N-(aminobutyl)-amidohexanoic acid]paclitaxel ester (Taxamine 3) | $-CO-(CH_2)_4-CO-NH-(CH_2)_4-NH_2$ |
| 9) 2'-[N-(aminopentyl)-amidohexanoic acid]paclitaxel ester (Taxamine 4) | $-CO-(CH_2)_4-CO-NH-(CH_2)_5-NH_2$ |
| 10) 2'-[N-(aminohexyl)-amidohexanoic acid]paclitaxel ester (Taxamine 5) | $-CO-(CH_2)_4-CO-NH-(CH_2)_6-NH_2$ |
| 11) 2'-[N-(aminoethyl)-amidoheptanoic acid]-paclitaxel ester (Taxamine 6) | $-CO-(CH_2)_5-CO-NH-(CH_2)_2-NH_2$ |
| 12) 2'-[N-(aminopropyl)-amidoheptanoic acid]-paclitaxel ester (Taxamine 7) | $-CO-(CH_2)_5-CO-NH-(CH_2)_3-NH_2$ |
| 13) 2'-[N-(aminobutyl)-amidoheptanoic acid]-paclitaxel ester (Taxamine 8) | $-CO-(CH_2)_5-CO-NH-(CH_2)_4-NH_2$ |
| 14) 2'-[N-(aminopentyl)-amidoheptanoic acid]-paclitaxel ester (Taxamine 9) | $-CO-(CH_2)_5-CO-NH-(CH_2)_5-NH_2$ |
| 15) 2'-[N-(aminohexyl)-amidoheptanoic acid]-paclitaxel ester (Taxamine 10) | $-CO-(CH_2)_5-CO-NH-(CH_2)_6-NH_2$ |
| 16) 2'-[N-(aminoethyl)-amidooctanoic acid]-paclitaxel ester (Taxamine 11) | $-CO-(CH_2)_6-CO-NH-(CH_2)_2-NH_2$ |
| 17) 2'-[N-(aminopropyl)-amidooctanoic acid]-paclitaxel ester (Taxamine 12) | $-CO-(CH_2)_6-CO-NH-(CH_2)_3-NH_2$ |
| 18) 2'-[N-(aminobutyl)-amidooctanoic acid]-paclitaxel ester (Taxamine 13) | $-CO-(CH_2)_6-CO-NH-(CH_2)_4-NH_2$ |
| 19) 2'-[N-(aminopentyl)-amidooctanoic acid]-paclitaxel ester (Taxamine 14) | $-CO-(CH_2)_6-CO-NH-(CH_2)_5-NH_2$ |
| 20) 2'-[N-(aminohexyl)-amidooctanoic acid]-paclitaxel ester (Taxamine 15) | $-CO-(CH_2)_6-CO-NH-(CH_2)_6-NH_2$ |
| 21) 2'-[N-(aminoethyl)-amidononanoic acid]-paclitaxel ester (Taxamine 16) | $-CO-(CH_2)_7-CO-NH-(CH_2)_2-NH_2$ |
| 22) 2'-[N-(aminopropyl)-amidononanoic acid]-paclitaxel ester (Taxamine 17) | $-CO-(CH_2)_7-CO-NH-(CH_2)_3-NH_2$ |
| 23) 2'-[N-(aminobutyl)-amidononanoic acid]-paclitaxel ester (Taxamine 18) | $-CO-(CH_2)_7-CO-NH-(CH_2)_4-NH_2$ |
| 24) 2'-[N-(aminopentyl)-amidononanoic acid]-paclitaxel ester (Taxamine 19) | $-CO-(CH_2)_7-CO-NH-(CH_2)_5-NH_2$ |
| 25) 2'-[N-(aminohexyl)-amidononanoic acid]-paclitaxel ester (Taxamine 20) | $-CO-(CH_2)_7-CO-NH-(CH_2)_6-NH_2$ |
| 26) 2'-[N-(aminoethyl)-amidodecanoic acid]-paclitaxel ester (Taxamine 21) | $-CO-(CH_2)_8-CO-NH-(CH_2)_2-NH_2$ |
| 27) 2'-[N-(aminopropyl)-amidodecanoic acid]-paclitaxel ester (Taxamine 21) | $-CO-(CH_2)_8-CO-NH-(CH_2)_3-NH_2$ |
| 28) 2'-[N-(aminobutyl)-amidodecanoic acid]- | $-CO-(CH_2)_8-CO-NH-(CH_2)_4-NH_2$ |

TABLE I-continued

| Compound | R |
|---|---|
| paclitaxel ester (Taxamine 22) | |
| 29) 2'-[N-(aminopentyl)-amidodecanoic acid]-paclitaxel ester (Taxamine 23) | —CO—(CH$_2$)$_8$—CO—NH—(CH$_2$)$_5$—NH$_2$ |
| 30) 2'-[N-(aminohexyl)-amidodecanoic acid]-paclitaxel ester (Taxamine 24) | —CO—(CH$_2$)$_8$—CO—NH—(CH$_2$)$_6$—NH$_2$ |
| Amino acid derivatives of 2'-(hexanedioic acid)-paclitaxel monoester where X is | —CO—(CH$_2$)$_4$—CO—NH—CHX—COOH |
| 31) aspartate | —CH$_2$COOH |
| 32) asparagine | —CH$_2$CONH$_2$ |
| 33) glutamate | —CH$_2$CH$_2$COOH |
| 34) glutamine | —CH$_2$CH$_2$CONH$_2$ |
| 35) glycine | —H |
| 36) serine | —CH$_2$OH |
| Amino acid derivatives of 2'-(heptanedioic acid)-paclitaxel monoester where X is | —CO—(CH$_2$)$_5$—CO—NH—CHX—COOH |
| 37) aspartate | —CH$_2$COOH |
| 38) asparagine | —CH$_2$CONH$_2$ |
| 39) glutamate | —CH$_2$CH$_2$COOH |
| 40) glutamine | —CH$_2$CH$_2$CONH$_2$ |
| 41) glycine | —H |
| 41) serine | —CH$_2$OH |
| Amino acid derivatives of 2'-(octanedioic acid)-paclitaxel monoester where X is | —CO—(CH$_2$)$_6$—CO—NH—CHX—COOH |
| 43) aspartate | —CH$_2$COOH |
| 44) asparagine | —CH$_2$CONH$_2$ |
| 45) glutamate | —CH$_2$CH$_2$COOH |
| 46) glutamine | —CH$_2$CH$_2$CONH$_2$ |
| 47) glycine | —H |
| 48) serine | —CH$_2$OH |
| Amino acid derivatives of 2'-(nonanedioic acid)-paclitaxel monoester where X is | —CO—(CH$_2$)$_7$—CO—NH—CHX—COOH |
| 49) aspartate | —CH$_2$COOH |
| 50) asparagine | —CH$_2$CONH$_2$ |
| 51) glutamate | —CH$_2$CH$_2$COOH |
| 52) glutamine | —CH$_2$CH$_2$CONH$_2$ |
| 53) glycine | —H |
| 54) serine | —CH$_2$OH |
| Amino acid derivatives of 2'-(decanedioic acid)-paclitaxel monoester where X is | —CO—(CH$_2$)$_8$—CO—NH—CHX—COOH |
| 55) aspartate | —CH$_2$COOH |
| 56) asparagine | —CH$_2$CONH$_2$ |
| 57) glutamate | —CH$_2$CH$_2$COOH |
| 58) glutamine | —CH$_2$CH$_2$CONH$_2$ |
| 59) glycine | —H |
| 60) serine | —CH$_2$OH |

SYNTHESIS OF DERIVATIVES

Synthesis of Hexanedioic Acid, Heptanedioic Acid, Octanedioic Acid, and Nonanedioic Acid Monoesters Four (4) dioic acid paclitaxel derivatives, still in accordance with the present invention, were synthesized. To do so, 20 mg of paclitaxel dissolved in 100 μl of pyridine is added to 40 mg of hexanoic, heptanoic, octanoic or nonanoic anhydride dissolved in 300 μl of methylene chloride. The mixture is allowed to react at room temperature for 5 hours. The solvent is evaporated and the pellet redissolved in methanol. Purification is performed by RP chromatography on a Pfp column [7.80/300 mm ](Phenomenex). The system used is the Waters 625 LC system and a 996 photodiode array detector. The product is eluted with a gradient of acetonitrile (0.5%) acetic acid:water:methanol running from 10-60-30 to 60-10-30 in 35 minutes. As shown in FIG. 1, the retention time of the new products were respectively 25.983 minutes for 2'-(hexanedioic acid)-paclitaxel monoester (Product 1), 28.733 minutes for 2'-(octanedioic acid)-paclitaxel monoester(Product 3) while being 24.433 minutes for paclitaxel.

Synthesis of 2'-(Decanedioic Acid)-paclitaxel Monoester

To 20 ml of decanedioic acid is added 20 mg of 1,1'-carbonyl-diimidazole in 100 μl of pyridine. The mixture was then transferred to 20 mg of paclitaxel dissolved in 100 μl of pyridine. After 12 hours of reaction the solvent is evaporated, the products dissolved in methanol and purified by RP chromatography as described above. As shown in FIG. 1, the retention time of 2'-(decanedioic acid)-paclitaxel monoester (Product 5) was 29.967 minutes.

Synthesis of Amido Derivatives of Paclitaxel

Figure 2:
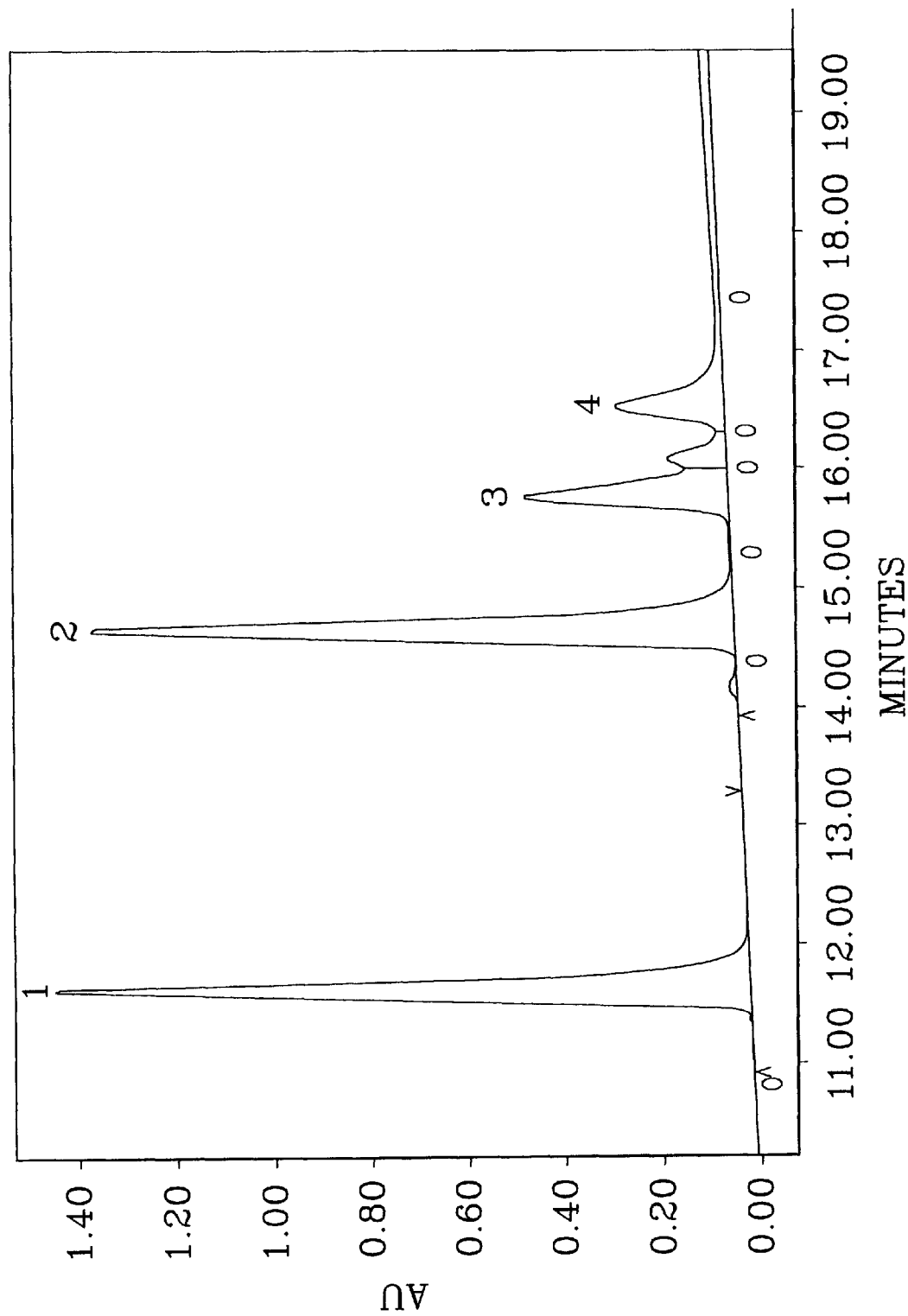
FIG. 2 illustrates a chromatography elution of 2'-(hexanedioic acid)-glutamate paclitaxel, paclitaxel, 2'-[N-(aminohexyl)-amidohexanoic acid]paclitaxel ester and 2'[N-(aminoethyl)-amidohexanoic acid]-paclitaxel ester.

Twenty-four (24) amido derivatives, still in accordance with the present invention, were synthesized. Briefly, 10 mg of Product 1, 2, 3, 4 or 5 are dissolved in 200 μl of acetonitrile and allowed to react with 2.5 equivalents of 1,1μ-carbonyl-diimidazole for 2 hours at 50° C. After cooling to room temperature, 100 μl of N,N-dimethylformamide were added and then 10 equivalents of ethylenediamine.2HCl, propanediamine, butanediamine, pentanediamine or hexanediamine.2HCl dissolved in water were also added. After an incubation of 4 hours, 5 ml of methylene chloride were added and the mixture was washed twice with water. The organic phase was saved and evaporated. The products were then purified by reverse phase chromatography on a Pfp column (7.80×300 mm, Phenomenex). The system used was the Waters 625 LC system connected to a 996 photodiode array detector. The product was eluted with a gradient of acetonitrile:water:methanol running from 20-50-30 to 70-00-30 in 20 minutes. As shown in FIG. 2, the retention time of 2'-[N-(aminohexyl)-amidohexanoic acid]-paclitaxel ester (Taxamine 5) was 15.795 minutes and 2'-[N-(aminoethyl)-amidohexanoic acid]-paclitaxel ester (Taxamine 1) was 16.562 minutes.

Amino Acid Derivatives of Dioic Acid Paclitaxel Monoesters

Thirty (30) amino acid derivatives, still in accordance with the present invention, were synthesized. The first step consisted in synthesizing the dioic acid paclitaxel monoesters as described above (Products 1, 2, 3, 4 or 5). To a solution of 2'-dioic acid paclitaxel monoesters (2–8 nmoles) in acetonitrile, was added a 10–20 fold excess of carbonyl diimidazole (CDI). The mixture was heated to 45° C. for twenty minutes and left to stand at room temperature overnight. A large excess (50 fold) of the amino acids asparagine, aspartate, glutamate, glutamine, glycine, or serine, dissolved in water was added, slowly over a period of twenty minutes, and the reaction proceeded at room temperature overnight.

Small quantities were purified on HPLC. A Waters 625 LC system with a 996 photodiode array detector was used. The products were eluted with a gradient of acetonitrile:water:methanol running from 20-50-30 to 70-00-30 in 20 minutes. As shown in FIG. 2, the retention time of 2'-(hexanedioic acid)-glutamate paclitaxel (Product 33) was 11.67 minutes.

Synthesis of Immunoconjugates

First an amido paclitaxel derivative is activated with glutaraldehyde. To do so, 1 mg of the derivative, prepared as mentioned above, is dissolved in 200 µl of methanol. Then, 100 µl of DMSO and 200 µl of PBS (Phosphate Buffer Saline) are added, followed by an additional 1 ml of DMSO. 60 µl of glutaraldehyde 25% is then slowly added to the solution and the mixture is gently stirred for 15 minutes. The reaction is monitored by thin layer chromatography and stopped by the addition of 5 ml of dichloromethane.

Second, the excess of glutaraldehyde is removed by 6 liquid extractions with aqueous solutions. The first one is performed with one volume of water. Four additional washes are then performed with a glycine:bicarbonate buffer pH 8.0 and the final wash with water. All aqueous fractions are discarded. The organic phase, which contains the activated compound, is dried in vacuo and stored at −80° C.

Third, the activated compound is then linked to an antibody. To do so, the antibody is dissolved in PBS and the activated paclitaxel derivative-glutaraldehyde is solubilized in a solution of methanol:DMSO (1:1) and 0.2% of Triton X-100™. This latter solution is then slowly added to the antibody solution in order to get a ratio of one molecule of antibody for 10 molecules of the activated compound. The mixture is stirred and incubated at 37° C. for one hour. The resulting immunoconjugate paclitaxel derivative-glutaraldehyde-antibody) is purified on a PD10™ column (Amersham Pharmacia).

Cytotoxicity of Derivatives

The cytotoxicity activity of the derivatives was evaluated on CCL6 cell line. The cells were maintained in RPMI 1640 supplemented with fetal calf serum 10% at 37° C., under a 5% $CO_2$ atmosphere.

Cells were plated at 2500 cells per well in 96 well plates. Drugs or derivatives were added 24 hours later. After three days of incubation with drugs or derivatives, 10 µl of Alamar Blue were added to the medium. The Alamar assay was performed as described by Pagé et al. (Pagé, B., et al., *Int. J. Oncol.*, 3, 473–476, 1993), and the $ID_{50}$ was calculated.

TABLE 2

Cytotoxicity of the new paclitaxel derivative on CCL6 cells

| Drugs tested | relative ID*<br>CCL6 |
| --- | --- |
| paclitaxel | 1 |
| 2'-(hexanedioic acid)-paclitaxel monoester (Product 1) | 33 |
| 2'-(decanedioic acid)-paclitaxel monoester (Product 5) | 20 |
| 2'-(hexanedioic acid)-glutamate-paclitaxel (Product 33) | 33 |
| 2'-[N-(aminoethyl)-amidohexanoic acid]-paclitaxel monoester (Taxamine 1) | 24 |
| 2'-[N-(aminohexyl)-amidohexanoic acid]-paclitaxel monoester | 13 |

*Relative ID: Ratio ID50 of derivative/ID50 of paclitaxel

Solubility of Derivatives

To evaluate the solubility of the derivatives in water, the procedure as described by Swindell et al. was followed (Swindell, C. S., et al., *J. Med. Chem.*, 34, 1176–1184, 1991). Each compound was distributed between a two-phase mixture of chloroform-water and octanol-water respectively. The samples were mixed vigorously for one hour, and after separation of the two phases, each phase was examined by HPLC. (Table 3)

TABLE 3

Proportion of derivatives, 2'-(hexanedioic acid) glutamate paclitaxel, 2'-(hexanedioic acid) paclitaxel monoester and 2'-[N-(aminoethyl)-amidohexanoic acid]-paclitaxel ester, in organic and aqueous phases following extraction with chloroform and octanol

|  |  | 2'-(hexanedioic acid) glutamate paclitaxel | 2'-(hexanedioic acid) paclitaxel monoester | 2'-[N-(aminoethyl)-amidohexanoic acid]-paclitaxel ester |
| --- | --- | --- | --- | --- |
| Chloroform extraction | Organic phase/aqueous phase | <10⁻³ | 115 | 151 |
| Octanol extraction | Organic phase/aqueous phase | n/a | 68 | n/a |

The present invention will be more readily understood by referring to the following examples, which are given to illustrate the invention rather than to limit its scope.

EXAMPLE 1

Synthesis of 2'-(Hexanedioic Acid)-paclitaxel Monoester (Product 1) and 2'-(Octanedioic Acid)-paclitaxel Monoester (Product 3)

To 3 ml of acetic anhydride in a 10 ml round bottom flask is added 500 mg of hexanedioic or octanedioic acid. The mixture is refluxed for 90 minutes. After reaction, the excess of acetic acid is evaporated under vacuum and the product recrystallised from chloroform, filtrated and dried.

To 20 mg of paclitaxel dissolved in 100 µl of pyridine is added 40 mg of hexanoic anhydride dissolved in 300 µl of methylene chloride. The mixture is allowed to react at room temperature for 5 hours. The solvent is evaporated and the pellet redissolved in methanol. Purification is performed by RP chromatography on a Pfp column [7.80/300 mm] (Phenomenex). The system used is the Waters 625 LC system and a 996 photodiode array detector. The product is eluted with a gradient of acetonitrile (0.5%) acetic acid:water:methanol running from 10-60-30 to 60-10-30 in 35 minutes. The retention time of the new products were respectively 25.983 minutes for 2'-(hexanedioic acid)-paclitaxel monoester and 28.733 minutes for and 2'-(octanedioic acid)-paclitaxel monoester, while being 24.433 minutes for paclitaxel.

EXAMPLE 2

Synthesis of 2'-(Decanedioic Acid)-paclitaxel Monoester (Product 5)

To 20 ml of decanedioic acid is added 20 mg of 1,1'-carbonyl-diimidazole in 100 µl of pyridine. The mixture was then transferred to 20 mg of paclitaxel dissolved in 100 µl of pyridine. After 12 hours of reaction the solvent is evaporated, the products dissolved in methanol and purified by RP chromatography as described above. The retention time of the new product was 29.967 minutes.

EXAMPLE 3

Synthesis of Amido Derivatives of Paclitaxel

Twenty-four (24) amido derivatives, still in accordance with the present invention, were synthesized. Briefly, 10 mg of Product 1, 2, 3, 4 or 5 are dissolved in 200 µl of acetonitrile and allowed to react with 2.5 equivalents of 1,1'-carbonyl-diimidazole for 2 hours at 50° C. After cooling to room temperature, 100 µl of N,N-dimethylformamide were added and then 10 equivalents of ethylenediamine.2HCl, propanediamine, butanediamine, pentanediamine or hexanediamine.2HCl dissolved in water were also added. After an 35 incubation of 4 hours, 5 ml of methylene chloride were added and the mixture was washed twice with water. The organic phase was saved and evaporated. The products were then purified by reverse phase chromatography on a Pfp column (7.80×300 mm, Phenomenex). The system used was the Waters 625 LC system connected to a 996 photodiode array detector. The product was eluted with a gradient of acetonitrile:water:methanol running from 20-50-30 to 70-00-30 in 20 minutes. As shown in FIG. 2, the retention time of 2'-[N-(aminohexyl)-amidohexanoic acid]-paclitaxel ester (Taxamine 5) was 15.795 minutes and 2'-[N-(aminoethyl)-amidohexanoic acid]-paclitaxel ester (Taxamine 1) was 16.562 minutes.

EXAMPLE 4

Synthesis of Amino Acid Derivatives of Dioic Acid Paclitaxel Monoesters

The amino acid derivatives were synthesized according to the following method: 10 mg of hexanedioic acid, octanedioic acid or decanedioic acid paclitaxel monoesters (2–8 nmoles) in acetonitrile, was added to a 10–20 fold excess of carbonyl diimidazole (CDI). The mixture was heated to 45° C. for twenty minutes and left to stand at room temperature overnight. A large excess (50 fold) of the amino acids asparagine, aspartate, glutamate, glutamine, glycine, or serine, dissolved in water was added, slowly over a period of twenty minutes, and the reaction proceeded at room temperature overnight.

Small quantities were purified on HPLC. A Waters 625 LC system with a 996 photodiode array detector was used. The products were eluted with a gradient of acetonitrile:water::methanol running from 20-50-30 to 70-00-30 in 20 minutes. As shown in FIG. 2, the retention time of 2'-(hexanedioic acid)-glutamate paclitaxel(Product 33) was 11.67 minutes.

EXAMPLE 5

Synthesis of Immunoconjugates

First a amido paclitaxel derivative is activated with glutaraldehyde. To do so, 1 mg of the derivative, prepared as mentionned above, is dissolved in 200 µl of methanol. Then, 100 µl of DMSO and 200 µl of PBS (Phosphate Buffer Saline) are added, followed by an additional 1 ml of DMSO. 60 µl of glutaraldehyde 25% is then slowly added to the solution and the mixture is gently stirred for 15 minutes. The reaction is monitored by thin layer chromatography and stopped by the addition of 5 ml of dichloromethane.

Second, the excess of glutaraldehyde is removed by 6 liquid extractions with aqueous solutions. The first one is performed with one volume of water. Four additional washes are then performed with a glycine: bicarbonate buffer pH 8.0 and the final wash with water. All aqueous fractions are discarded. The organic phase, which contains the activated compound, is dried in vacuo and stored at −80° C.

Third, the activated compound is then linked to an antibody. To do so, the antibody is dissolved in a mixture of PBS, glycerol and DMSO in proportions of 60-20-20. The activated 2'-glurarylhexanediamine paclitaxel-glutaraldehyde dissolved in DMSO is then slowly added to the antibody solution in order to get a ratio of one molecule of antibody for 10 molecules of the activated compound. The mixture is stirred and incubated at room temperature for three hours and the resulting immunoconjugate is purified on a PD-10™ column (Amersham Pharmacia).

Figure 3:
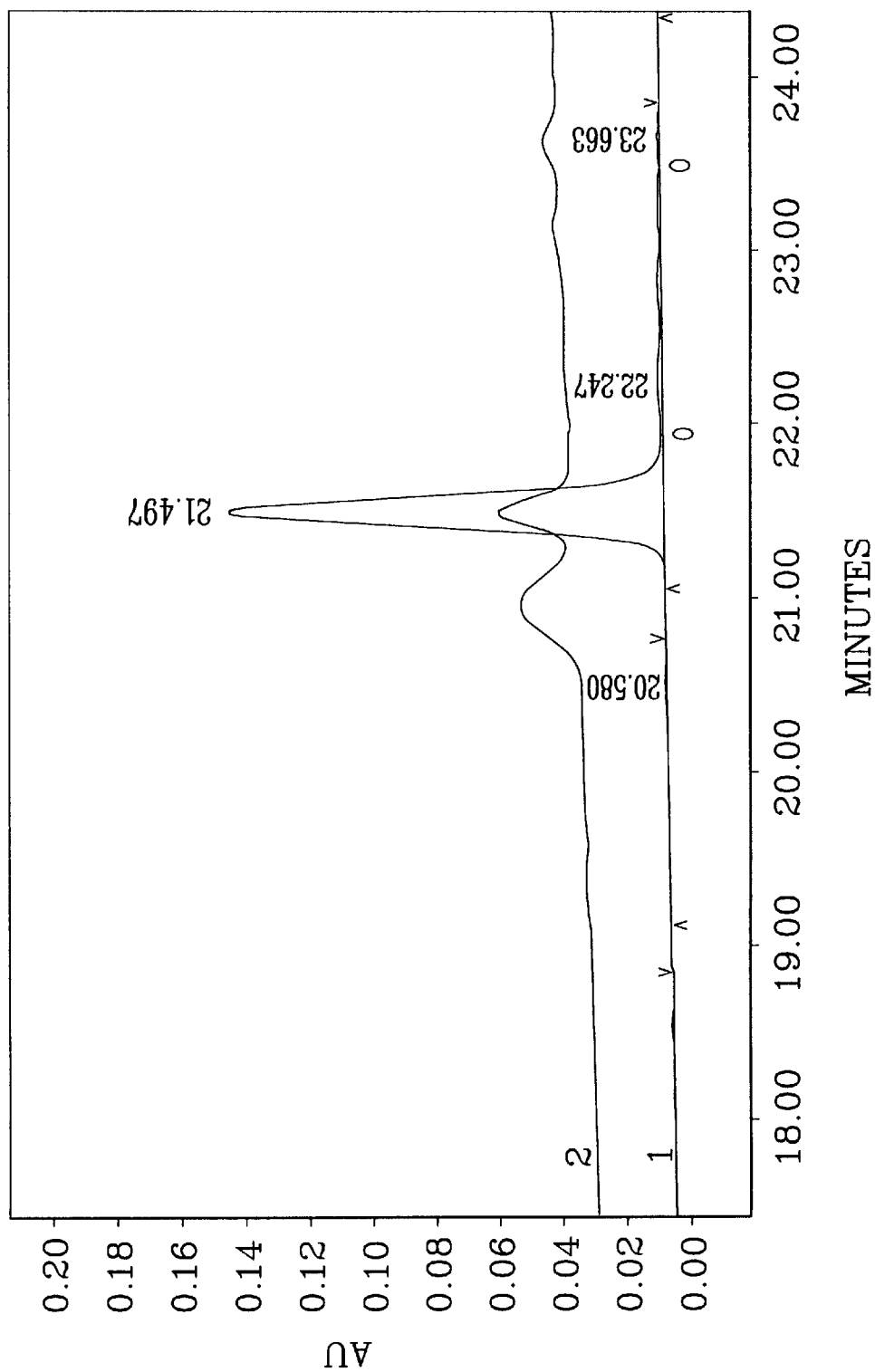
FIG. 3 illustrates elution profile of paclitaxel (1) in comparison with a hydrolyzed immunoconjugate (2) according to a preferred embodiment of the invention.

To calculate the rate of conjugation, an aliquot of the immunoconjugate containing known amount of antibody is hydrolysed by incubation overnight in a 0.1 M $KHCO_3$ buffer. The mixture is then extracted three times with equal volume of ethyl acetate. The organic phase is evaporated. The pellet is dissolved in a minimum volume of methanol and assayed by HPLC (FIG. 3). The amount of drug in the immunoconjugate is calculated according to a standard curve of paclitaxel. As seen in FIG. 3, the retention time of both compounds is 21.49 minutes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of preparing compounds of Formula II:

$$R={=}(CH){-}(CH_2)_m{-}(R_1)_n{-}(CH_2)_p{-}(CH){=}M \qquad II$$

wherein $R_1$ is

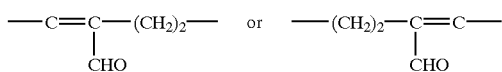

and wherein
  m and p are an integer varying from 0 to 3, with one of m and p being 0;
  n is an integer varying from 1 to 3;
  M is selected from the group consisting of a peptide containing a lysine and linked to the carbon atom depicted in Formula II via the amino group of the lysine and a protein containing a lysine and linked to the carbon atom depicted in Formula II via the amino group of the lysine; and R represents a new derivative of paclitaxel having Formula I

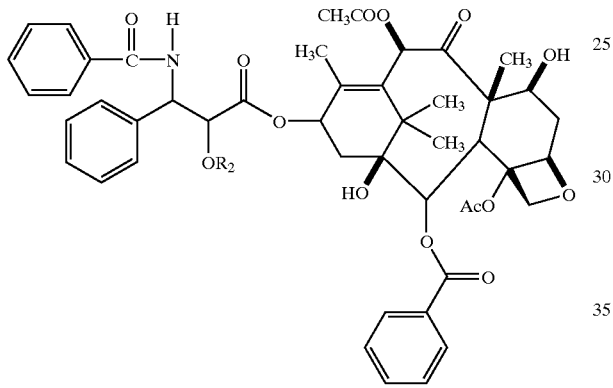

wherein $R_2$ is a —CO—$(CH_2)_{4-8}$—COX, in which X is selected from the group consisting of a hydroxyl, a 1,2-diaminoethenyl, a 1,3-diaminopropyl, a 1,4-diaminobutyl, a 1,5-diaminopentyl, a 1,6-diaminohexyl, and a polar amino acid residue; which derivative is attached to the carbon atom depicted in Formula II by its $R_2$ residue; said method comprising the steps of:
  a) reacting said derivative of paclitaxel with glutaraldehyde to obtain an intermediate complex; and
  b) reacting the intermediate complex of step a) with a protein or a peptide to obtain an immunoconjugate.

2. The method of claim 1, wherein m is 3 when p is 0.
3. The method of claim 1, wherein m is 0 when p is 3.
4. The method of claim 1, further comprising between step a) and b) a step of purifying the complex obtained in step a).
5. The method of claim 4, further comprising after step b) a step of purifying the immunoconjugate.
6. The method of claim 1, wherein M is a protein selected from the group of BCM43 monoclonal antibody, BCM43 humanized antibody, BCM43 chimerized antibody, the (Fab), (Fab)$_2$ or scFv moiety of the BCM43 antibody, BCM17 monoclonal antibody, BCM17 humanized antibody, BCM17 chimerized antibody, the (Fab), (Fab)$_2$ or scFv moiety of the BCM17 antibody, anti-carcinoembryonic monoclonal antibody and anti-alphafetoprotein monoclonal antibody.

7. A compound of Formula II $$R={=}(CH){-}(CH_2)_m{-}(R_1)_n{-}(CH_2)_p{-}(CH){=}M \qquad II$$

wherein $R_1$ is

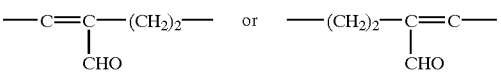

and wherein
  m and p are an integer varying from 0 to 3, with one of m and p being 0;
  n is an integer varying from 1 to 3;
  M is selected from the group consisting of a peptide containing a lysine and linked to the carbon atom depicted in Formula II via the amino group of the lysine and a protein containing a lysine and linked to the carbon atom depicted in Formula II via the amino group of the lysine; and R represents a new derivative of paclitaxel having Formula I

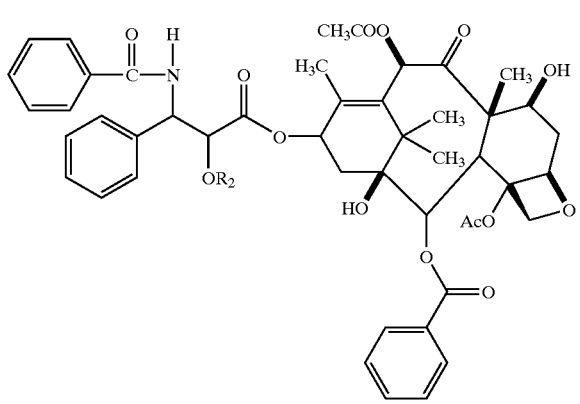

wherein $R_2$ is a —CO—$(CH_2)_{4-8}$—COX, in which X is selected from the group consisting of a hydroxyl, a 1,2-diaminoethenyl, a 1,3-diaminopropyl, a 1,4-diaminobutyl, a 1,5-diaminopentyl, a 1,6-diaminohexyl, and a polar amino acid residue; which derivative is attached to the carbon atom depicted in Formula II by its $R_2$ residue.

8. The compound of claim 7, wherein m is 3 when p is 0.
9. The compound of claim 7, wherein m is 0 when p is 3.
10. The compound of claim 7, wherein M is a protein selected from the group of BCM43 monoclonal antibody, BCM43 humanized antibody, BCM43 chimerized antibody, the (Fab), (Fab)$_2$ or scFv moiety of the BCM43 antibody, BCM17 monoclonal antibody, BCM17 humanized antibody, BCM17 chimerized antibody, the (Fab), (Fab)$_2$ or scFv moiety of the BCM17 antibody, anti-carcinoembryonic monoclonal antibody and anti-alphafetoprotein monoclonal antibody.
11. A method for treating cancer which comprises administering to a patient a therapeutic dosage of a compound of Formula II as defined in claim 7.
12. A pharmaceutical composition comprising a compound of formula II as defined in claim 7, and a pharmaceutically acceptable carrier.

* * * * *